US007797052B2

(12) United States Patent
Chiang

(10) Patent No.: US 7,797,052 B2
(45) Date of Patent: Sep. 14, 2010

(54) BI-DIRECTION TREATING DEVICE WITH PLAYER FUNCTION

(76) Inventor: Chih-Cheng Chiang, 8F-2, No. 61, Sec. 2, Gongyi Rd., Taichung City (TW)

( * ) Notice: Subject to any disclaimer, the term of this patent is extended or adjusted under 35 U.S.C. 154(b) by 203 days.

(21) Appl. No.: 12/022,576

(22) Filed: Jan. 30, 2008

(65) Prior Publication Data

US 2009/0192419 A1 Jul. 30, 2009

(51) Int. Cl.
*A61N 1/00* (2006.01)

(52) U.S. Cl. ........................................................ 607/76

(58) Field of Classification Search ................... 607/76, 607/44, 69
See application file for complete search history.

(56) References Cited

U.S. PATENT DOCUMENTS 5,903,211 A * 5/1999 Flego et al. ............ 340/286.07
6,077,237 A * 6/2000 Campbell et al. ........... 600/587
6,285,905 B1 * 9/2001 Chiang et al. .................. 607/2
2006/0258289 A1 * 11/2006 Dua .......................... 455/41.3
2007/0250145 A1 * 10/2007 Kraus et al. ................ 607/136

* cited by examiner

*Primary Examiner*—Mark W Bockelman
*Assistant Examiner*—Roland Dinga
(74) *Attorney, Agent, or Firm*—Apex Juris, pllc; Tracy M Heims

(57) ABSTRACT

A bi-direction treating device with player function including a power supplying unit, a controller, a displaying unit, an audio outputting unit, an input unit, a multimedia processing unit and a high voltage treating unit where device is supplied by the power supplying unit and is operated by user through inputting operation instructions from the input unit. The controller controls the multimedia processing unit and the high voltage treating unit according to user's instructions. And, through the displaying unit, the audio outputting unit and the high voltage treating unit, the user can enjoy a multimedia acousto-optical effect during treatment.

10 Claims, 8 Drawing Sheets

BI-DIRECTION TREATING DEVICE WITH PLAYER FUNCTION

FIELD OF THE INVENTION

The present invention is related to an electronic medical instrument, and more particularly to an electronic medical instrument which can output high voltage electromagnetic for stimulating both hands and any other acupuncture points.

BACKGROUND OF THE INVENTION

Please refer to FIG. 1 and FIG. 2. According to traditional Chinese medical science, on the hands and feet, there are reactive reflection regions 1 of acupuncture points corresponding to all kinds of organs, such as, acupuncture point of sciatic nerve 2 and acupuncture point of common cold 3, and this theory has already commonly applied to treat various diseases. However, people always worry that infection might happen since the needle of acupuncture is used by many people. Accordingly, the instrument by using electricity to stimulate human acupuncture points is developed.

Please refer to FIG. 3. As described above, the acupuncture points on the hands and feet are corresponding to all kinds of organs, that's because, a conductive route, named as meridian line 4, 5, is connected between the acupuncture point and the hand or the foot. Therefore, when one person is going to have pathological change, the acupuncture point on the hand will have a positive reaction. That's because when patient feels hurt, impedance will be generated so as to change the micro-circulation magnetic field of the patient. Consequently, the electromagnetic field produced by current can use to diagnosis the organ which is on the point of getting pathological change, so as to facilitate treatment. Although this kind of treating method can achieve the effect of prophylaxis and health care, the treating procedure is quite boring, which obviously will influence using desire and reduce produce value.

SUMMARY OF THE INVENTION

Therefore, the object of the present invention is to provide a bi-directional device with function, so that when the user is treated thereby, he or she can simultaneously enjoy a multimedia acousto-optical effect, thereby increasing the using desire and also the product value.

The present invention is related to a bi-direction treating device with player function including a power supplying unit, a high voltage treating unit, a displaying unit, an audio outputting unit, a multimedia processing unit, an input unit and a controller. The power supplying unit is used to convert the voltage from an external power source into a desired voltage for supplying each unit. The high voltage treating unit has an electronic oscillation generator, two output terminals and an electrode set. The electronic oscillation generator inputs voltage for outputting an oscillated current at two output terminals. The electrode set has two output points which are respectively connected to the two output terminals.

Accordingly, through the input unit, the user can initiate the high voltage treating unit and the multimedia processing unit, and through attaching two output points of the electrode set to human body and moving to each portion and acupuncture point of human body, the treating can be processed. And, through the displaying unit and the audio outputting unit, the user can enjoy a multimedia acousto-optical effect during treatment.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DESCRIPTION OF THE PREFERRED EMBODIMENT

Figure 1:
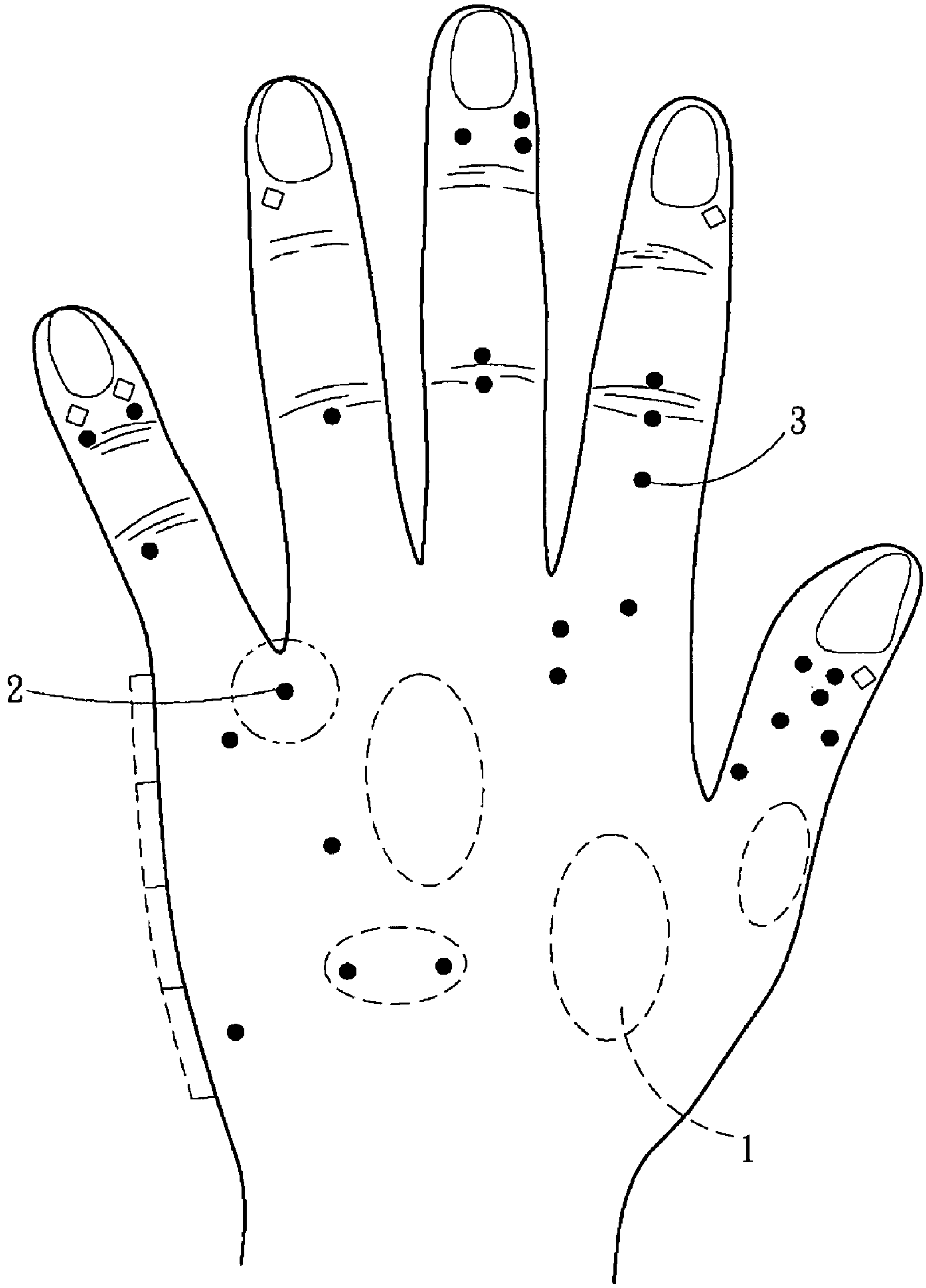
Fig. 1 PRIOR ART
FIG. 1 is a schematic view showing the reactive reflection region of acupuncture points on the back of hand.
Figure 2:
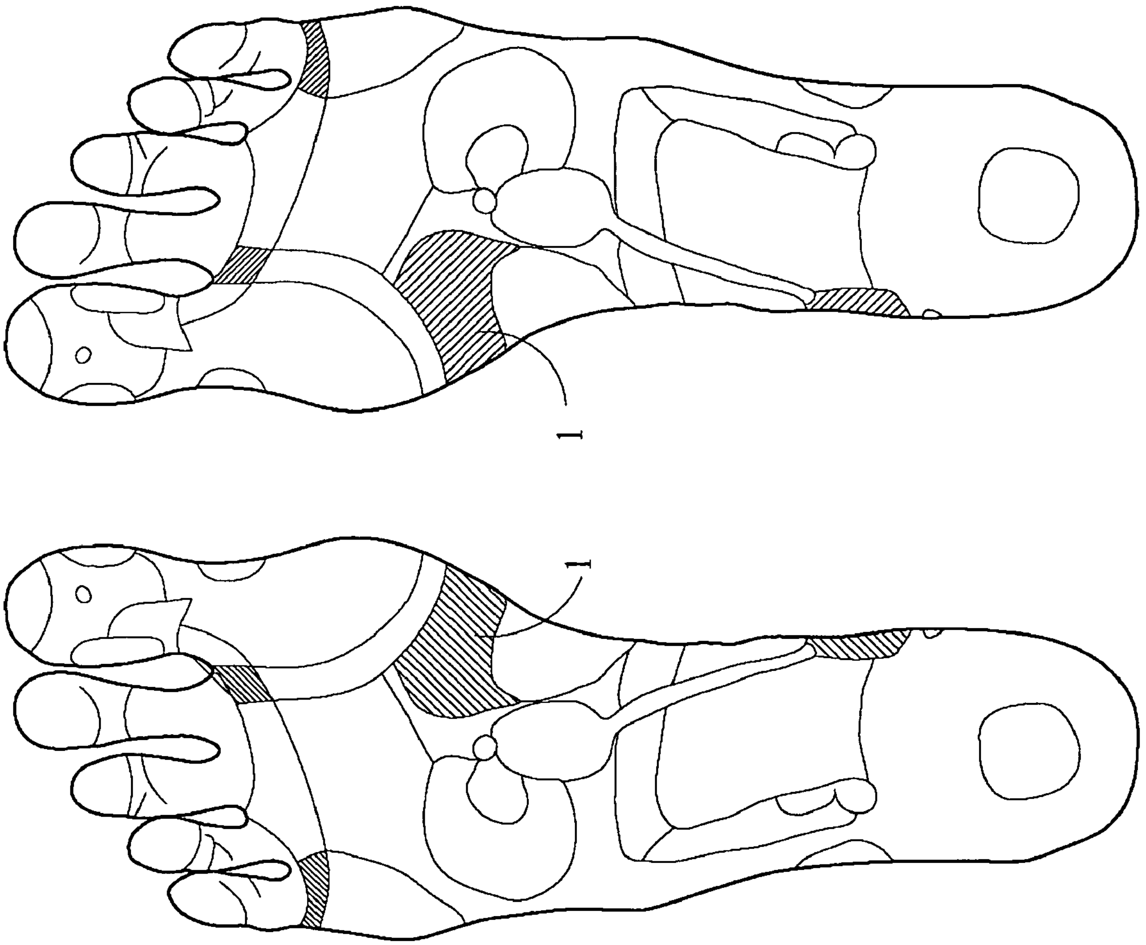
Fig. 2 PRIOR ART
FIG. 2 is a schematic view showing the reactive reflection region of acupuncture point at the soles of feet.
Figure 3:
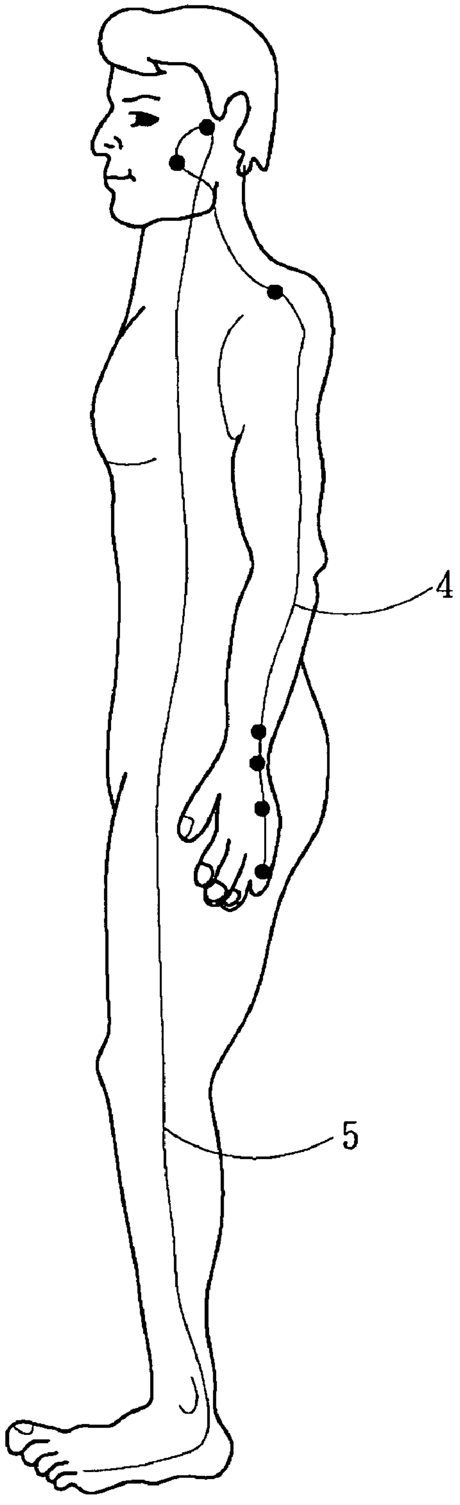
Fig. 3 PRIOR ART
FIG. 3 is a schematic view showing the meridian of human body.
Figure 4:
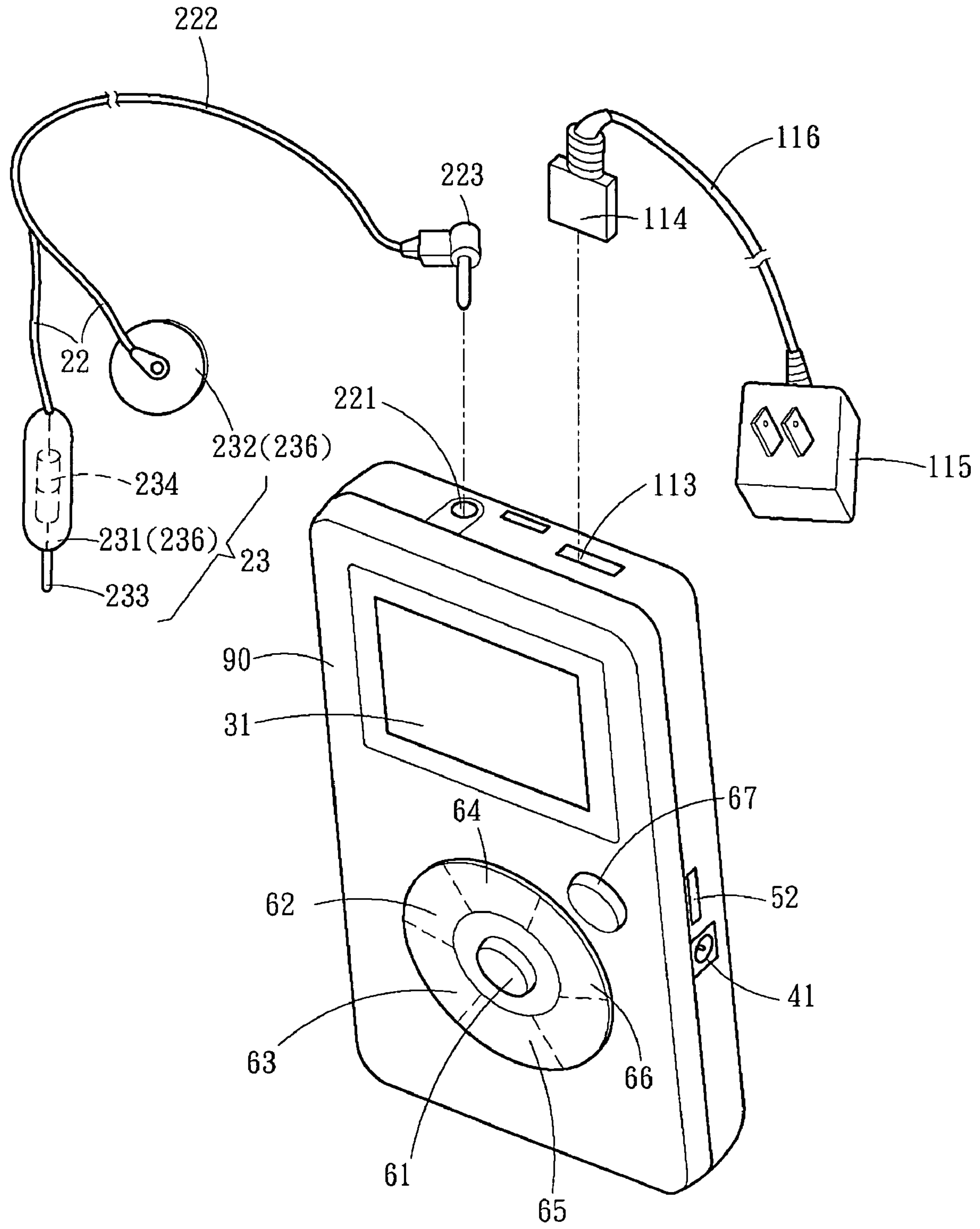
FIG. 4 is an appearance view of the present invention.
Figure 5A:
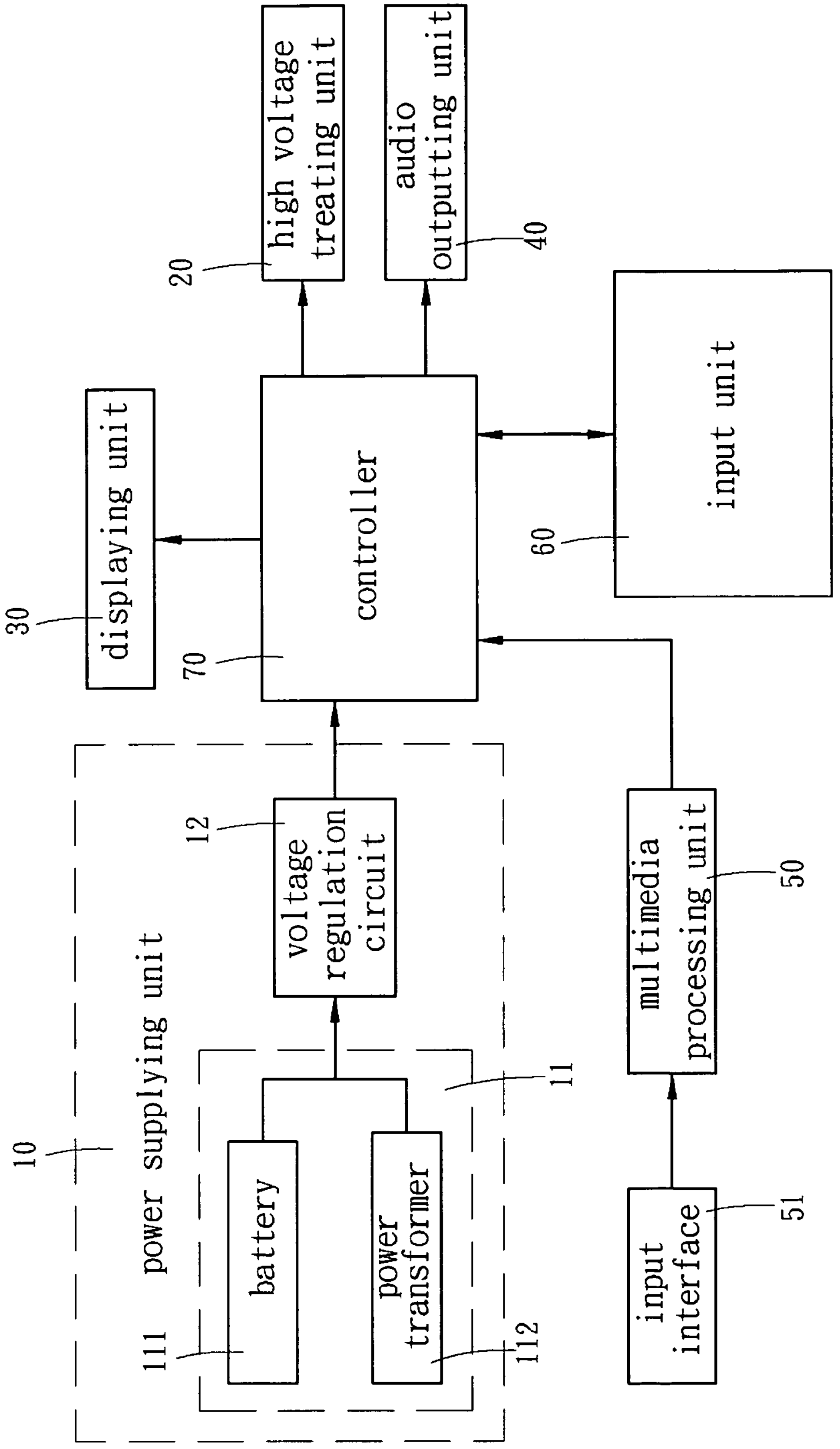
FIG. 5A is a block diagram showing the function of the present invention.

Please refer to FIG. 4 and FIG. 5A. The present invention is related to a bi-direction treating device including a power supplying unit 10, a high voltage treating unit 20, a displaying unit 30, an audio outputting unit 40, a multimedia processing unit 50, an input unit 60 and a controller 70, and a housing 90 having all these units mounted therein. The power supplying unit 10 is used to convert the voltage of an external power source 11 into a desired voltage for supplying each unit, and the external power source 11 can be one of a battery 111 and a power transformer 112, wherein the battery 111 is convenient for carrying and the power transformer 112 facilitates lasting power supply. The housing 90 has a power plugging hole 113 for electrically connecting to the power transformer 112, so as to obtain power from mains electricity through a power plug 114, a mains plug 115 and a power line 116, and further, for protecting the safety of circuit, the power supplying unit 10 also includes a voltage regulation circuit 12 for providing stable voltage supply.

Figure 5B:
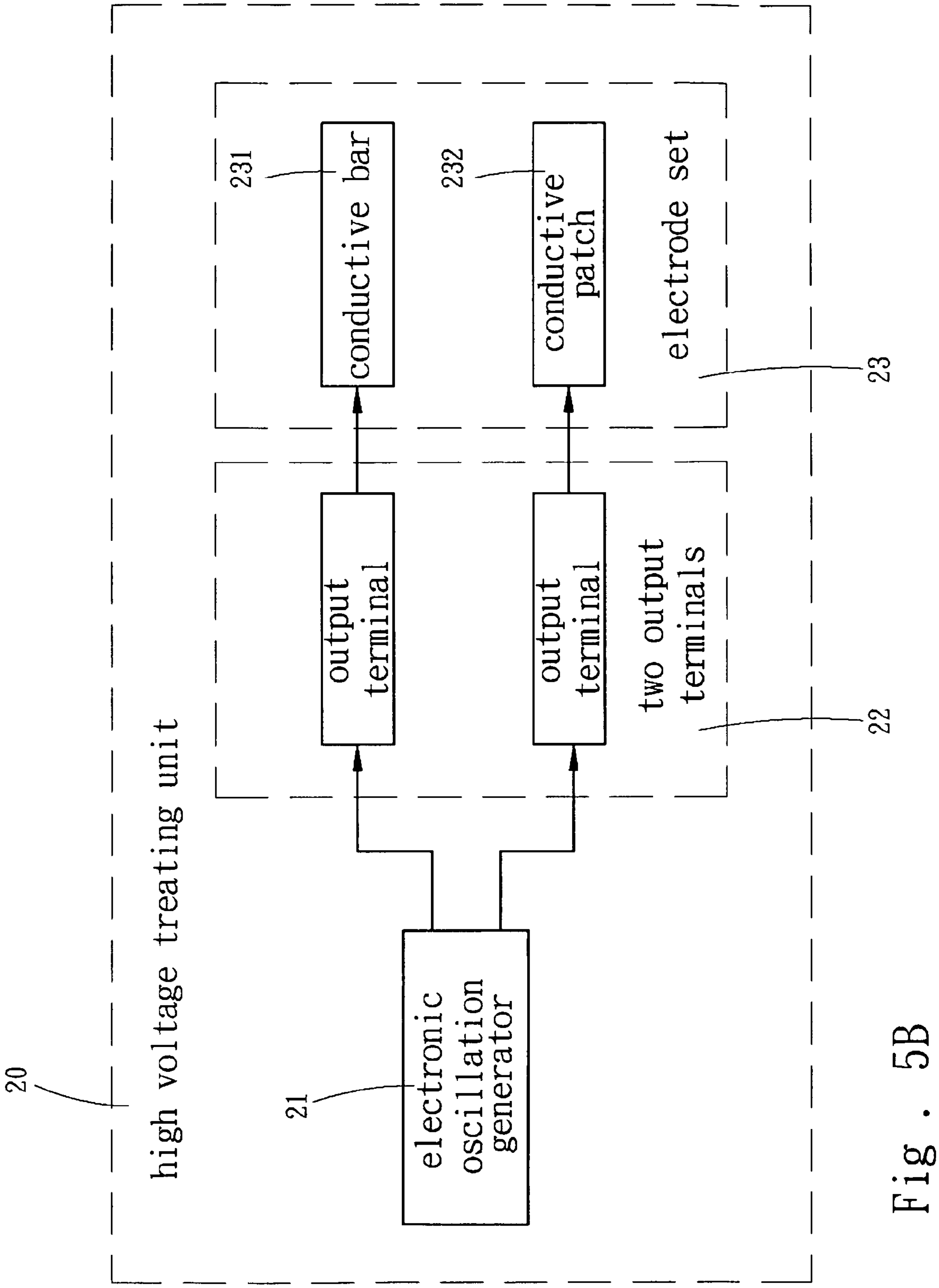
FIG. 5B is another block diagram showing the function of the present invention.
Figure 6:
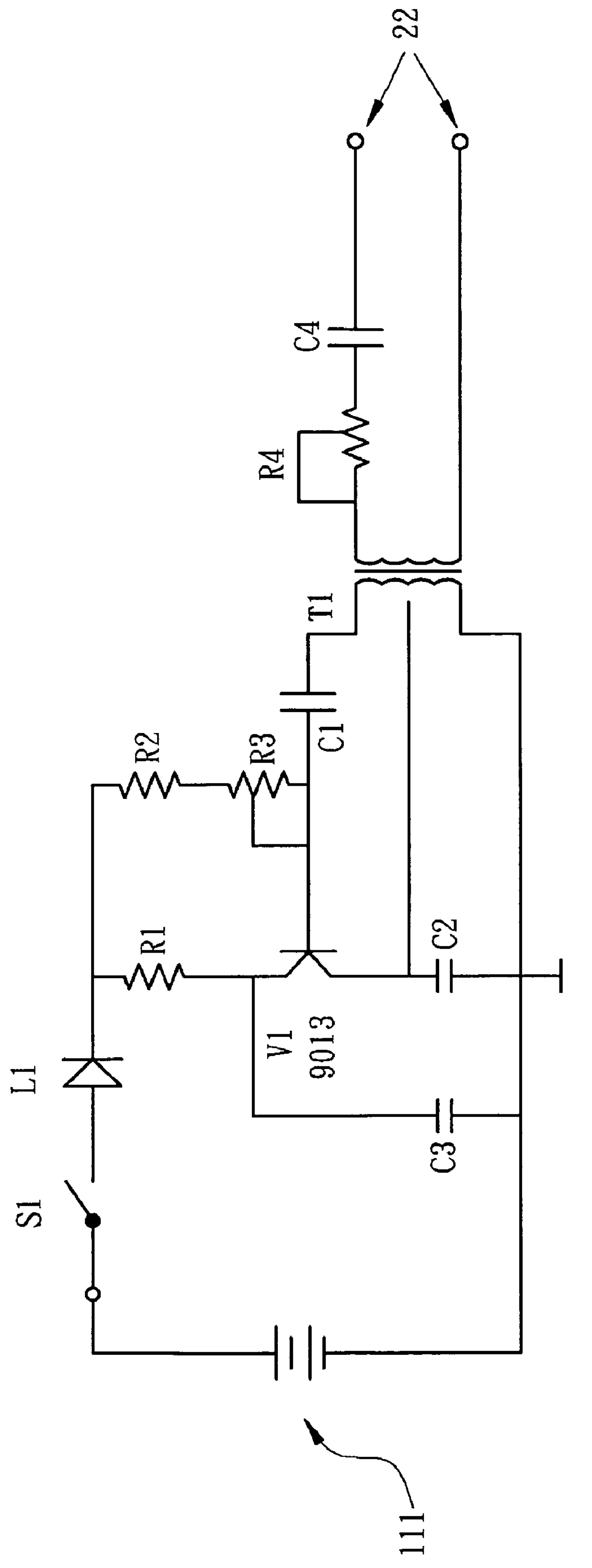
FIG. 6 is a circuit diagram showing an electronic oscillator of the present invention.

Please refer to FIG. 5B and FIG. 6. The high voltage treating unit 20 has an electronic oscillation generator 21, two output terminals 22 and an electrode set 23. The electronic oscillation generator 21 inputs voltage for outputting an oscillated current at two output terminals 22, wherein the power from the battery 111 or a DC power converted from the AC power from the power transformer 112 passes a switch S1 used for switching power, a LED (Light-Emitting Diode) L1 for displaying the operation situation, resistors R1, R2, power variable resistors R3, R4, capacitors C1, C2, C3, C4, a transistor V1 and a transformer T1, so that through the electronic oscillation generator 21, the voltage can output an oscillated current at two output terminals 22.

The electrode set 23 has two output points 236 and can be composed by conductive bar 231 and conductive patch 232 which are respectively connected to the two output terminals 22. The two output terminals 22 are connected to the conductive bar 231 and the conductive patch 232 through an output opening on the housing 90, a connector 223, and a Y-shaped connecting wire 222. The front end of the conductive bar 231 is an electrode 233 formed by electromagnetic material, and the electrode 233 has plural magnets 234 mounted at the back thereof for converting the current outputted from the output terminals 22 into magnetic wave, which is then conducted to the electrode 233 and outputted by the front end of the conductive bar 231.

Figure 7:
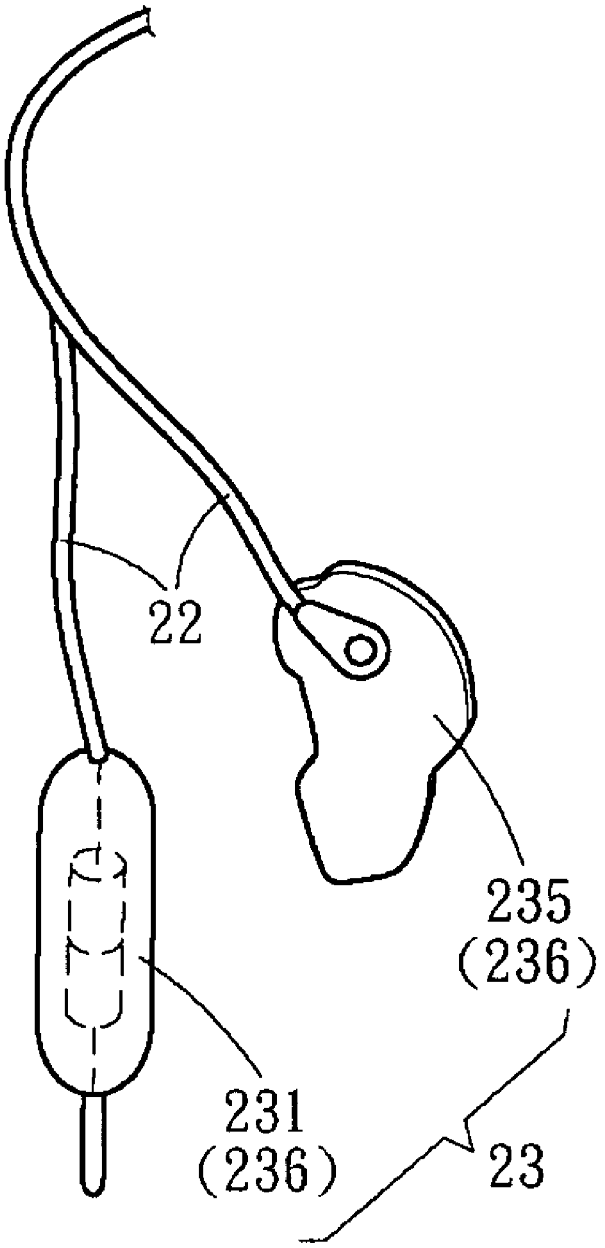
FIG. 7 is schematic view showing the electrode set in an embodiment of the present invention.

Please refer to FIG. 7. The two output points 236 of the electrode set 23 can be composed by conductive bar 231 and conductive auricle patch 235, which are identically connected to the two output terminals 22. Here, the auricle patch 235 is attached to the ear of human body.

The displaying unit 30 is used for outputting images for showing on a screen 31 on the housing 90. The audio outputting unit 40 is used for outputting sounds and the housing 90 has an audio output opening 41 for connecting with acoustic equipment (not shown) or earphones (not shown). The multimedia processing unit 50 is used to processing multimedia data for generating video signal and audio signal respectively to the displaying unit 30 and the audio outputting unit 40. The multimedia processing unit 50 can be MP3 controller or MP4 controller for playing music or film, or can be a controller for processing other kinds of multimedia data only if the multimedia data can be processed and converted into video signal and audio signal. For facilitating data input, the multimedia processing unit 50 further includes an input interface 51, which can be USB (Universal Serial Bus) or memory slot interface, wherein the housing 90 may need a slot 52 for plugging the memory, and the USB interface and the power plugging hole 113 can be integrated, so that the power plugging hole 113 can be plugged by other devices with USB interface for connection and data acquisition.

The input unit 60 is used for inputting operation instructions which can be circular buttons with different input functions at different positions. The input unit 60 includes a power switch 61 for switching power, an increment button 62 and a decrement button 63 for adjusting output strength and a time setting button 64 for setting operation time. It should be notice that the input unit 60 also can use the input interface 51 to adjust the operation of the multimedia processing unit 50 and the high voltage treating unit 20, for example, the increment button 62 can increase the strength of the treating electromagnetic wave or increase the sound volume, and so as the decrement button 63 and the time setting button 64.

Furthermore, the input unit 60 also can include a diagnosis button 65 and a treating button 66. The diagnosis button 65 and the treating button 66 can respectively let the high voltage treating unit 20 provide outputs at specific strengths for diagnosis and treating, and the user can switch therebetween through pressing the buttons, for example, the user can use the device to diagnosis that which portion thereof should be treated and then switch to the treating mode for treating. Besides, the input unit 60 can further include a multimedia power switch 67 for independently controlling the operation of the multimedia processing unit 50, so that the multimedia function can be paused when the user doesn't need it.

The controller 70 is connected to the power supplying unit 10, the high voltage treating unit 20, the displaying unit 30, the audio outputting unit 40, the multimedia processing unit 50 and the input unit 60. The controller 70 is the core of the whole system and can control the operation of different units in accordance with the input instructions from the input unit 60, so as to satisfy individual demands.

In the aforesaid, the present invention provides the user the input unit 60 for initiating the high voltage treating unit 20 and the multimedia processing unit 50. When treating, the conductive patch 232 is attached on the ear and the electrode 233 is moved to different portions of human body and acupuncture points. At the same time, through the displaying unit 30 and the audio outputting unit 40, the user can enjoy the audio and video provided by the multimedia processing unit 50. Therefore, according to the present invention, the user can enjoy multimedia function during treating, so as to avoid from feeling boring and also increase the using desire.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A bi-directional treating device with player function, comprising:

a power supplying unit, for converting an external power source into a desired voltage;

a high voltage treating unit, having an electronic oscillation generator, two output terminals and an electrode set, wherein the electronic oscillation generator inputs voltage for outputting an oscillated current at two output terminals, the electrode set has two output points and the two output points are respectively connected with the two output terminals;

a displaying unit, for outputting image;

an audio outputting unit, for outputting sound;

a multimedia processing unit, for processing multimedia data so as to generate video signal and audio signal respectively to the displaying unit and the audio outputting unit;

an input unit, for inputting operation instructions; and a controller, connected to the power supplying unit, the high voltage treating unit, the displaying unit, the audio outputting unit, the multimedia processing unit and the input unit, for controlling thereof in accordance with the operation instructions inputted by the input unit.

2. The bi-directional treating device as claimed in claim 1, wherein the multimedia processing unit is one of a MP3 player and a MP4 player.

3. The bi-directional treating device as claimed in claim 1, wherein the multimedia processing unit further comprises an input interface.

4. The bi-directional treating device as claimed in claim 3, wherein the input interface is one of an USB (Universal Serial Bus) and a memory slot interface.

5. The bi-directional treating device as claimed in claim 1, wherein the external power source is one of a battery and a power transformer.

6. The bi-directional treating device as claimed in claim 1, wherein the power supplying unit further comprises a voltage regulation circuit.

7. The bi-directional treating device as claimed in claim 1, wherein the input unit comprises a power switch, an increment button, a decrement button and a time setting button.

8. The bi-directional treating device as claimed in claim 1, wherein the input unit comprises a diagnosis button and a treating button which are respectively pressed for letting the high voltage treating unit provide outputs in specific strengths for diagnosis and treating.

9. The bi-directional treating device as claimed in claim 1, wherein the input unit further comprises a multimedia power switch for independently controlling the operation of the multimedia processing unit.

10. The bi-directional treating device as claimed in claim 1, wherein the two output points of the electrode set are one set of conductive bar and conductive patch and conductive bar and conductive auricle patch, and wherein the front end of the conductive bar is made of electromagnetic material, the electrode has plural magnets at the back side thereof for converting the current outputted at the output terminal into magnetic wave and conducting thereof to the electrode.

* * * * *